United States Patent [19]

Kleinschroth et al.

[11] Patent Number: 5,489,608
[45] Date of Patent: Feb. 6, 1996

[54] INDOLOCARBAZOLE DERIVATIVES AND THE USE THEREOF

[75] Inventors: Jurgen Kleinschroth, Denzlingen; Johannes Hartenstein, Stegen-Wittental; Christoph Schachtele, Freiburg; Claus Rudolph, Vorstetten, all of Germany

[73] Assignee: Goedecke Aktiengesellschaft, Berlin, Germany

[21] Appl. No.: 382,959

[22] Filed: Feb. 2, 1995

Related U.S. Application Data

[63] Continuation of Ser. No. 39,541, Mar. 29, 1993, abandoned, which is a continuation of Ser. No. 828,532, Jan. 24, 1992, abandoned, which is a continuation-in-part of Ser. No. 632,224, Dec. 19, 1990, abandoned.

[30] Foreign Application Priority Data

Dec. 21, 1989 [DE] Germany .................. 39 42 296.8

[51] Int. Cl.⁶ .......................... A61K 31/40; C07D 487/14
[52] U.S. Cl. ............................. 514/410; 548/416
[58] Field of Search ............... 548/416; 514/410

[56] References Cited

U.S. PATENT DOCUMENTS 4,912,107  3/1990  Kleinschroth et al. ............. 514/232.5

OTHER PUBLICATIONS

Magnus et al, "Indole –2,3–Quinodimethanes, etc" Tetrahedron, 40 (14) pp. 2795–2797 (1984).

*Primary Examiner*—Patricia L. Morris
*Attorney, Agent, or Firm*—Elizabeth M. Anderson

[57] ABSTRACT

The present invention provides indolocarbazole derivatives of the formula

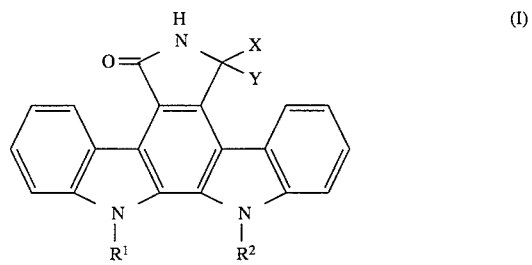

as well as the regioisomeric mixtures thereof, pharmacologically acceptable salts thereof, processes for the preparation thereof, and pharmaceutical compositions containing them for the treatment and/or prophylaxis of heart and blood vessel diseases, such as thromboses, arterioscleroses, hypertonias, of bronchopulmonary diseases, inflammatory processes, allergies, cancers and degenerative damage of the central nervous system, and for the treatment of viral diseases.

7 Claims, No Drawings

INDOLOCARBAZOLE DERIVATIVES AND THE USE THEREOF

This is a continuation of Ser. No. 08/039,541, filed Mar. 29, 1993, now abandoned. It is to be noted that Ser. No. 087/039,541 is a continuation of Ser. No. 07/828,532 filed Jan. 24, 1992 and abandoned, which is a C-I-P of Ser. No. 07/632,224 filed Dec. 19, 1990, which is also abandoned.

BACKGROUND OF THE INVENTION

Protein kinase C plays an important key role for intracellular signal transduction and is closely linked with the regulation of contractile, secretory, and proliferative processes.

DESCRIPTION OF THE INVENTION

The present invention concerns new indolocarbazole derivatives of formula I

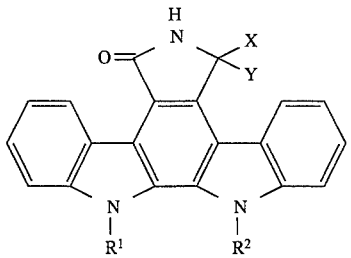

or a pharmaceutically acceptable salt thereof wherein one of $R^1$ and $R^2$ is hydrogen or a straight-chained or branched alkyl containing from 1 to 6 carbon atoms and the other of $R^1$ and $R^2$ is a straight-chained or branched cyanoalkyl, cyanoalkoxyalkyl, cyanoalkylthioalkyl, isocyanoalkyl, carboxyalkyl, azidoalkyl, amidinoalkyl, amidinothioalkyl, (2-nitroguanidino)alkyl, isocyanatoalkyl or isothiocyanatoalkyl containing, in each case, from 1 to 6 carbon atoms or is a radical of formula $-(CH_2)_2-CO-NR^3R^4$, in which $R^3$ and $R^4$ are each independently hydrogen, alkyl of from 1 to 4 carbon atoms or benzyl and X and Y are either the same and both represent hydrogen atoms or X and Y are different, one of X and Y is hydrogen atom and the other is hydroxyl or alkoxy containing from 1 to 4 carbon atoms.

The present invention also concerns processes for the preparation of compounds of formula (I) and of regioisomeric mixtures of two of these compounds of formula (I), as well as pharmaceutical compositions containing at least one compound of formula (I) and methods of using the compounds or regioisomeric mixtures thereof.

Compounds of formula (I) are preferred wherein one of $R^1$ and $R^2$ is hydrogen or methyl, ethyl, propyl or isopropyl and the other of $R^1$ and $R^2$ is cyanomethyl, 2-cyanoethyl, 2-cyanopropyl, 3-cyanopropyl, carboxymethyl, 2-carboxyethyl or 3-carboxypropyl and X and Y both are hydrogen.

Compounds of formula (I) are especially preferred wherein one of $R^1$ and $R^2$ is methyl or ethyl and the other of $R^1$ and $R^2$ is cyanomethyl, 2-cyanoethyl, 2-cyanopropyl, 3-cyanopropyl, carboxymethyl, 2-carboxyethyl or 3-carboxypropyl radical and X and Y are both hydrogen.

The following compounds are especially preferred:
12-(2-cyanoethyl)-6,7,12,13-tetrahydro-13-methyl-5-oxo-5 H-indolo[2,3-a]pyrrolo[3,4-c]carbazole (Example 2),
13-(2-cyanoethyl)-6,7,12,13-tetrahydro-12-methyl-5-oxo-5H-indolo[2,3 -a]pyrrolo [3,4-c]carbazole,
12-(3-azidopropyl)-6,7,12,13-tetrahydro-5-oxo-5-indolo[2,3-a]pyrrolo[3,4-c]carbazole,
13-(3-azidopropyl)-6,7,12,13-tetrahydro-5-oxo-5-indolo[2,3-a]pyrrolo[3,4-c]carbazole,
12-(3-azidopropyl)-6,7,12,13-tetrahydro-5-oxo-5H-indolo[2,3-a]pyrrolo[3,4-c]carbazole, and
13-(3-azidopropyl)-6,7,12,13-tetrahydro-5-oxo-5H-indolo[2,3-a]pyrrolo[3,4-c]carbazole.

The regioisomeric mixtures of these compounds are also especially preferred.

The preparation of the compounds of formula (I) takes place, depending upon the substitution, according to one of the following processes:

A) The substitution on the carbazole nitrogen atoms of indolocarbazole derivatives of formula (I), in which one of $R^1$ and $R^2$ is hydrogen or of known indolocarbazoles of the formula (II) (for the preparation thereof, see U.S. Ser. No. 484,445 filed Feb. 20, 1990),

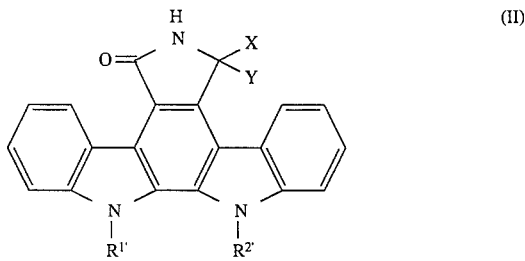

wherein X and Y have the above meanings and $R^{1'}$ and $R^{2'}$ are hydrogen or one of $R^{1'}$ and $R^{2'}$ is hydrogen and the other of $R^{1'}$ and $R^{2'}$ is a straight-chained or branched alkyl containing from 1 to 6 carbons, can be carried out in a known manner for the N-substitution of indoles and carbazoles. Thus, for example, a straight-chained or branched alkyl containing from 1 to 6 carbons can be introduced into a compound of formula (I), in which one of $R^1$ and $R^2$ is hydrogen, by first converting this compound into an alkali metal derivative, for example a sodium derivative, for example by reacting with an alkali metal hydride, such as sodium hydride, and then reacting the derivative obtained with a compound of the formula III

$$R^5-Z \qquad (III)$$

wherein $R^5$ is a straight-chained or branched alkyl containing from 1 to 6 carbons and Z is preferably a halogen atom, especially a chlorine, bromine or iodine atom.

Compounds of formula (I), in which $R^1$ or $R^2$ is methyl or ethyl, can also be prepared in known manner by alkylation with dimethyl or diethyl sulphate.

In an analogous manner, compounds of the formula (II), in which $R^{1'}$, $R^{2'}$, X and Y have the above given meanings, can be reacted with compounds of the formula (III), in which $R^5$ is a straight-chained or branched cyanoalkyl, cyanoalkoxyalkyl, cyanoalkylthioalkyl, isocyanoalkyl or azidoalkyl radical and Z has the above-given meaning, to produce compounds of the formula (I), in which one of $R^1$ or $R^2$ has one of the meanings given for $R^5$.

Further functional modification of the introduced radicals $R^1$ or $R^2$ can also be carried out in known manner. Thus, for example, an azidoalkyl radical can be converted by catalytic hydrogenation into an aminoalkyl radical and this subjected to further functional modifications, for example by the preparation of an isothiocyanatoalkyl radical by reaction with 1,1'thiocarbonyldiimidazole. Compounds of the formula (I), in which one of the radicals $R^1$ or $R^2$ is carboxyalkyl, are preferably prepared in known manner by saponification of compounds of formula (I), in which one of $R^1$ or $R^2$ is alkoxycarbonylalkyl (see U.S. Pat. No. 4,855,489).

B) Compounds of formula (I) are also obtained by the base-catalyzed Michael addition of indolocarbazoles of formula (II), in which X, Y, $R^{1'}$ and $R^{2'}$ have the above meanings, to activated olefins of the formula IV

wherein $R^6$ is hydrogen or a C1–C3-alkyl and $R^7$ is a cyano group or an unsubstituted or substituted carboxamide group.

C) Compounds of general formula (I), in which one of the radicals $R^1$ and $R^2$ is carboxyethyl or a radical of the formula —(CH$_2$)$_2$—CO—NR$^3$R$^4$, are also obtained by the base-catalyzed Michael addition of indolocarbazoles of the formula (II), in which the substituents have the above meanings, to acrylic acid esters containing from 1 to 7 carbon atoms, in known manner from compounds of the formula V

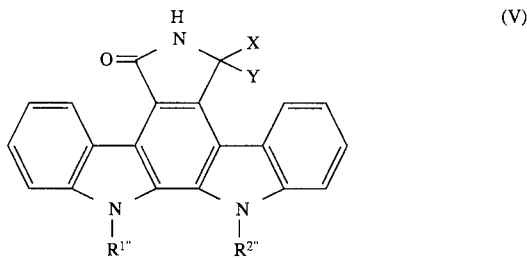

wherein X and Y have the above meanings and one of $R^{1''}$ and $R^{2''}$ is hydrogen or a straight-chained or branched alkyl containing from 1 to 6 carbons and one of $R^{1''}$ and $R^{2''}$ is alkoxycarbonylethyl containing from 1 to 7 carbons by amide formation (reaction with amines of the formula HNR$^3$R$^4$) or by saponification.

Thus, compounds of formula (I), in which one of $R^1$ and $R^2$ is carboxyalkyl, are preferably obtained by the acidic saponification of compounds of formula (I), in which one of the radicals $R^1$ or $R^2$ is a tert.butoxycarbonylalkyl.

As bases for the Michael addition according to process B) or C), alkali metal alkoxides, hydroxides or amides can be used, for example, sodium methylate, sodium hydroxide or sodamide; ammonia; secondary amines, for example diethylamine, diisopropylamine or piperidine; tertiary amines, for example triethylamine, pyridine or 1,8-diazabicyclo[5,4,0]undec-7-ene (DBU) and quaternary ammonium hydroxides or alkoxides. Appropriate solvents for the Michael addition include C1–C4-alcohols, for example methanol, ethanol and tert.-butanol; hydrocarbons, for example toluene; ethers, for example diethyl ether or dioxan; and acetonitrile. As base, it is preferred to use DBU and, as solvent, acetonitrile.

The Michael additions according to process B) or C), compounds of formula (I) are preferably obtained in which $R^2$ stands for the newly introduced radical.

D) Compounds of formula I, in which 1 of the substituents X or Y is hydrogen and the other substituent is hydroxy, may be prepared in known manner by oxidation of compounds of formula I, wherein X and Y are hydrogen, with lead tetraacetate in glacial acetic acid. If the oxidation is carried out in the presence of C1–C4 alcohols, compounds of formula I are obtained in which one of the substituents X or Y is hydrogen and the other substituent is C1–C4 alkoxy.

Insofar as regioisomeric mixtures are obtained according to the above-described processes, compounds of formula (I) can be used in the form of the regioisomeric mixtures or the regioisomers can be separated by known separation processes, for example crystallization or chromatography.

Compounds of formula (I) which have a chiral center can be used as stereoisomeric mixtures or in the form of the enantiomers. The enantiomers can be obtained by the processes conventionally employed for the optical separation of stereoisomers.

Acidic compounds of formula (I) can, if desired, be converted in known manner by treatment with an appropriate base, into a pharmaceutically usable salt. Inorganic bases, for example sodium, potassium or calcium salts, or organic bases, for example ethylenediamine or mono- or diethanolamine can be used.

Basic compounds of formula (I), which have a basic center on one of $R^1$ or $R^2$, are, for the purpose of purification and/or for galenical reasons, preferably converted into crystalline, pharmacologically acceptable salts. The salts are obtained in the usual way by neutralization of the bases with appropriate inorganic or organic acids. As acids, for example, hydrochloric acid, sulphuric acid, phosphoric acid, hydrobromic acid, acetic acid, tartaric acid, lactic acid, citric acid, malic acid, salicylic acid, ascorbic acid, malonic acid, fumaric acid, oxalic acid or succinic acid can be used.

The compounds of the present invention are potent inhibitors of protein kinases, such as protein kinase C (PKC). Thus, for example, the compound of Example 2 shows, in an enzyme assay of protein kinase C activated with phosphatidylserine and diacylglycerol, a 50% inhibition at a concentration of 20 nM. The experiment was carried out in the manner described in U.S. Pat. No. 4,855,489 hereby incorporated by reference (inhibition of protein kinase C).

Indolocarbazoles have been described as inhibitors of protein kinase C (see J. Antibiot. 1977, 30, 275; Biochem. Biophys. Res. Commun. 1986, 135, 197; Int. J. Cancer. 1989, 43, 851; U.S. Ser. No. 484,445, filed Feb. 20, 1990). The advantage of the compounds of formula (I) according to the present invention in comparison with the known indolocarbazole derivatives which have been described as inhibitors of protein kinase C lies in the high selectivity of the PKC inhibition, hitherto not described for this class of compounds, in comparison with the inhibition of other protein kinases, for example of the cAMP-dependent protein kinase (A-kinase), of the cGMP-dependent protein kinase (G-kinase), of the myosine light chain kinase (MLC-kinase) and of the tyrosine-specific kinase (T-kinase).

The superior selectivity of the compounds according to the present invention can be seen from the following Table 1, in which are listed the IC$_{50}$ values for the compound of Example 2, in comparison with the IC$_{50}$ values observed for the indolocarbazole glycoside staurosporine. As the comparison shows, in contradistinction to the non-selective inhibitor staurosporine, in the case of the compound of Example 2, an inhibition of the other protein kinases is first achieved at concentrations which lie more than 100 times above the concentrations necessary for the inhibition of PKC.

TABLE 1

| | Inhibition of Protein Kinases (IC$_{50}$, μM) | | | | |
|---|---|---|---|---|---|
| | PKC | A- | G- | MLC- | T-kinase |
| Example 2 | 0.020 | >100 | 6.2 | 5.8 | 25 |
| Staurosporine | 0.013 | 0.04 | 0.018 | 0.0096 | 0.006* |

*J. Antibiot. 1987; 40:1782

The determination of the inhibition of A-, G-, MLC- or T-kinase took place according to the processes described in the literature (see G. N. Gill and M. Walton, Advances in Cyclic Nucleotide Research, Vol. 10, published by G. Brooker and G. S. Robinson, Raven Press, New York, 1979; Eur. J. Biochem. 1986, 158, 203; Biochem. J. 1984, 218, 863; Analyt. Biochem. 1983, 135, 37; Mol. Immunol. 1989, 26, 897).

Protein kinase C plays an important key role for intracellular signal transduction and is closely linked with the regulation of contractile, secretory and proliferative processes.

Because of these properties, the compounds of the present invention can be used for the treatment and/or prophylaxis of heart and blood vessel diseases, for example thromboses, arterioscleroses, hypertonias, of bronchopulmonary diseases, inflammatory processes, allergies, cancers and degenerative damage of the central nervous system and for the treatment of viral diseases. Because of the high selectivity of the compounds according to the present invention, in the case of the therapy and/or prophylaxis of the above-mentioned diseases, fewer side effects are to be expected as a result of inhibition of other kinases.

The compounds of the instant invention can be administered enterally or parenterally in the appropriate formulation in doses of from 1 to 500 mg/kg, and preferably of from 1 to 50 mg/kg.

The compounds of formula (I) of the present invention can be administered orally or parenterally in liquid or solid form. As injection solution, water is preferably used which contains the additives usual in the case of injection solutions, such as stabilizing agents, solubilizing agents and/or buffers. Such additives include, for example, tartrate and citrate buffers, ethanol, complex formers (such as ethylenediaminetetraacetic acid and the non-toxic salts thereof), as well as high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycol). Compositions suitable for oral administration can, if desired, additionally contain flavoring and/or sweetening materials.

The following examples are given for the purpose of illustrating the present invention; they are not intended to limit its scope in any way.

EXAMPLE 1

12-(2-Cyanoethyl)-6,7,12,13-tetrahydro-5-oxo-5H-indolo[2,3-a]pyrrolo[3,4-c]carbazole 300 mg (0.96 mmole) 6,7,12,13-tetrahydro-5-oxo-5H-indolo[2.3-a]pyrrolo [3,4-c]carbazole, suspended in 20 mL acetonitrile, are mixed with 0.3 mL (4.56 mole) acrylic acid nitrile and 2 drops of 1,8-diazabicyclo[5,4,0[undec-7-ene (DBU) and stirred for 3 days at 20° C. The mixture of starting materials and product is filtered off, again mixed with the same amounts of acrylic acid nitrile, DBU and acetonitrile and stirred for a further 3 days at 20° C. After again repeating this procedure and after a further 3 days at 20° C., the 12-(2-cyanoethyl)-6,7,12, 13-tetrahydro-5-oxo-5H-indolo[2,3-a]pyrrolo[3,4-c]carbazole is filtered off in the form of beige colored crystals which decompose above 275° C.

EXAMPLE 2

12-(2-Cyanoethyl)-6,7,12,13-tetrahydro-13-methyl-5-oxo-5H-indolo[2,3-a]pyrrolo[3,4 -c]carbazole 36 mg (1.2 mmole) sodium hydride (80% in mineral oil) are suspended under an atmosphere of nitrogen in 50 mL dry dimethylformamide and 365 mg (1 mmole) 12-(2-cyanoethyl)-6,7,12,13-tetrahydro-5-oxo-5H-indolo[2,3-a]pyrrolo[3, 4-c]carbazole added portionwise thereto at ambient temperature. After subsidence of the gas evolution, stirring is continued for 1 hour at 20° C. 0.08 mL (1.25 mmole) methyl iodide is then added thereto and stirring continued for 16 hours at ambient temperature. The solvent is distilled off in a vacuum and the residue is chromatographed on silica gel with toluene/ethanol (95:5 v/v). The fraction with an $R_f$ of 0.3 in dichloromethane/methanol (95:5 v/v) is isolated and recrystallized from tetrahydrofuran. 12-(2-cyanoethyl)-6,7,12,13-tetrahydro-13 -methyl-5-oxo-5H-indolo[2,3-a]pyrrolo[3,4-c]carbazole is obtained in the form of pale yellow crystals which decompose above 270° C.

EXAMPLE 3

12-(2-Carboxyethyl)-6,7,12,13-tetrahydro-5-oxo-5H-indolo[2,3-a]pyrrolo[3,4-c]carbazole 147 mg (0.33 mmole) 12-(2-tert.-butoxycarbonylethyl)-6,7,12,13-tetrahydro-5-oxo-5H-indolo[ 2,3-a]pyrrolo[3,4-c]carbazole are stirred for 16 hours at 20° C. in 5 mL 18% hydrochloric acid and 5 mL dioxan and then for 2 hours at 50° C. The product formed is filtered off, washed with a little water and ethanol and dried in a vacuum at 90° C. 12-(2-Carboxyethyl)-6,7,12,13-tetrahydro-5-oxo-5H-indolo[ 2,3-a]pyrrolo[3,4-c]carbazole is obtained in the form of pale beige crystals which decompose above 320° C.

The 12-(2-tert.-butoxycarbonylethyl)-6,7,12,13-tetrahydro -5-oxo-5H-indolo[2,3-a]pyrrolo[ 3,4-c]carbazole was used as starting material is prepared as follows: 500 mg (1.6 mmole) 6,7,12,13-tetrahydro-5-oxo-5H-indolo[2,3-a]pyrrolo[ 3,4-c]carbazole, suspended in 50 mL acetonitrile, are mixed with 1.5 mL (11.2 mmole) tert.-butyl acrylate and 2 drops of DBU and stirred for 2 days at 20° C. The solvent is evaporated off and the residue partitioned between 500 mL ethyl acetate and 100 mL of water (undissolved starting material is filtered off). The ethyl acetate phase is separated off, dried over anhydrous sodium sulphate and evaporated. The residue is chromatographed on silica gel with toluene/ ethyl acetate (3:1 v/v). The fraction with an $R_f$ of 0.4 in dichloromethane/methanol (95:5 v/v) is isolated, stirred up with diisopropyl ether and the crystals are filtered off. There is obtained 12-(2-tert.butoxycarbonylethyl)-6,7,12,13-tetrahydro-5-oxo-5H-indolo[ 2,3-a]pyrrolo[3,4-c]carbazole in the form of pale beige crystals which decompose above about 185° C.

The 13-(2-tert.butoxycarbonylethyl)-6,7,12,13-tetrahydro-5-oxo-5H-indolo[2,3-a]pyrrolo[ 3,4-c]carbazole was also isolated in small amounts.

EXAMPLE 4

12-(2-Cyanoethyl)-6,7,12,13-tetrahydro-7-hydroxy-13 -methyl-5-oxo-5H-indolo[2,3-a]pyrrolo[3,4-c]carbazole 140 mg (0.37 mmole) 12-(2-cyanoethyl)-6,7,12,13 -tetrahydro-13-methyl-5-oxo-5H-indolo[2,3a]pyrrolo[3,4-c] carbazole (Example 2) are stirred for 2 days at 20° C. in 20 mL glacial acetic acid with 197 mg (0.44 mole) lead tetraacetate. The solvent is evaporated in a vacuum and the residue partitioned between 50 mL tetrahydrofuran and 50 mL of saturated sodium hydrogencarbonate solution. The tetrahydrofuran phase is separated, washed with saturated sodium chloride solution, dried over anhydrous sodium sulphate and evaporated. The residue is chromatographed on silica gel with toluene/ethyl acetate 95:5 (v/v) and dichloromethan/methanol 98:2 (v/v). The fraction with an $R_f$ of 0.1 in toluene/ethyl acetate 3:1 (v/v) is isolated. 12-(2-Cyanoethyl)-6,7,12,13-tetrahydro-7-hydroxy-13-methyl-5-oxo-5H-indolo[2,3-a]pyrrolo[3,4-c]carbazole is obtained in the form of beige crystals which decompose above about 220° C.

EXAMPLE 5

12-(2-Cyanoethyl)-6,7,12,13-tetrahydro-7-methoxy-13-methyl-5-oxo-5H-indolo[2,3-a]pyrrolo[3,4-c]carbazole 356 mg (0.94 mmole) 12-(2-cyanoethyl)-6,7,12,13-tetrahydro-13-methyl-5-oxo-5H-indolo[2,3a]pyrrolo[3,4-c]carbazole (Example 2) are stirred for 16 hours at 20° C. in 50 mL glacial acetic acid and 1 mL methanol. The further preparation is carried out in Example 4 and the crude product is chromatographed on silica gel with dichloromethane/methanol 199:1 (v/v). The fraction with an $R_f$ of 0.25 in toluene/ethyl acetate 4:1 (v/v) is isolated. 12-(2-Cyanoethyl)-6,7,12,13-tetrahydro-7-methoxy-13-methyl-5-oxo-5H-indolo[2,3-a]pyrrolo[3,4-c]carbazole is obtained in the form of beige crystals which decompose above about 200° C.

The following were made by methods analogous to the above procedures.

12(or 13)-(3-azidopropyl)-6,7,12,13-tetrahydro-5-oxo-5H-indolo[2,3-a]pyrrolo[3,4-c]carbazole (6:1 regioisomeric mixture), m.p. up from 230° C. decomp.

12(or 13)-(3-azidopropyl)-6,7,12,13-tetrahydro-5-oxo-5H-indolo[2,3-a]pyrrolo[3,4-c]carbazole (9:2 regioisomeric mixture), m.p. up from 210° C. decomp.

We claim:
1. A compound of formula

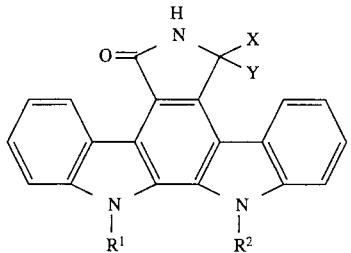

or a pharmaceutically acceptable salt thereof or a regioisomeric mixture thereof wherein one of $R^1$ and $R^2$ is a hydrogen or a straight or branched alkyl of from 1 to 6 carbon atoms and the other of $R^1$ and $R^2$ is a straight or branched carboxyalkyl, azidoalkyll, amidinoalkyl, amidinothioalkyl, (2-nitroguanidino) alkyl, containing in each case from 1 to 6 carbon atoms, or is —$(CH_2)_2$—CO—$NR^3R^4$ wherein $R^3$ and $R^4$ are each independently hydrogen, alkyl of from 1 to 4 carbon atoms or benzyl; and X and Y are each hydrogen or one of X and Y is hydrogen and the other is hydrogen or alkoxy of from 1 to 4 carbon atoms.

2. A compound according to claim 1, wherein one of $R^1$ and $R^2$ is hydrogen, methyl, ethyl, propyl or isopropyl and the other of $R^1$ and $R^2$ is carboxymethyl, 2-carboxyethyl or 3-carboxypropyl and X and Y are each hydrogen.

3. A compound according to claim 1, wherein one of $R^1$ and $R^2$ is methyl or ethyl and the other of $R^1$ and $R^2$ is carboxymethyl, 2-carboxyethyl or 3-carboxypropyl and X and Y are each hydrogen.

4. A compound selected from the group consisting of 12-(3-azidopropyl)-6,7,12,13-tetrahydro-5-oxo-5H-indolo[2,3-a]pyrrolo[3,4-c]carbazole, and 13-(3-azidopropyl)-6,7,12,13-tetrahydro-5-oxo-5H-indolo[2,3-a]pyrrolo[3,4-c]carbazole.

5. A pharmaceutical composition which comprises a therapeutically effective amount of a compound according to claim 1 in combination with a pharmaceutically acceptable carrier.

6. A method for treating or preventing diseases of the blood vessels and heart which comprises administering a therapeutically effective amount of a pharmaceutical composition according to claim 5 to a mammal in need thereof.

7. A compound of the formula 12-(2-carboxyethyl)-6,7,12,13-tetrahydro-5-oxo-5H-indolo[2,3-a]pyrrolo[3,4-c]carbazole.

* * * * *